United States Patent [19]

Boeck et al.

[11] 4,288,549
[45] Sep. 8, 1981

[54] METHOD OF PRODUCING THE A-30912 ANTIBIOTICS

[75] Inventors: LaVerne D. Boeck; Ralph E. Kastner, both of Indianapolis, Ind.

[73] Assignee: Eli Lilly and Company, Indianapolis, Ind.

[21] Appl. No.: 126,078

[22] Filed: Mar. 3, 1980

Related U.S. Application Data

[63] Continuation-in-part of Ser. No. 46,744, Jun. 8, 1979, abandoned.

[51] Int. Cl.³ .............................................. C12P 17/18
[52] U.S. Cl. ..................................... 435/119; 435/913
[58] Field of Search ................................... 435/119, 68

[56] References Cited

U.S. PATENT DOCUMENTS 4,024,245  5/1977  Hoehn et al. ....................... 424/119
4,024,246  5/1977  Higgens et al. ..................... 424/119

Primary Examiner—Lionel M. Shapiro
Attorney, Agent, or Firm—Nancy J. Harrison; Arthur R. Whale

[57] ABSTRACT

The microorganism *Aspergillus nidulans* var. *roseus* NRRL 11440 and the method of producing the A-30912 antibiotics by submerged aerobic fermentation of this microorganism to give the A-42355 antibiotic complex. A-30912 factors A, B, D, and H are separated from the A-42355 complex by chromatography. The A-42355 complex and A-30912 factors A, B, D, and H are antifungal agents.

7 Claims, 2 Drawing Figures

METHOD OF PRODUCING THE A-30912 ANTIBIOTICS

CROSS-REFERENCE TO RELATED APPLICATION

This is a continuation-in-part application of our co-pending application Ser. No. 46,744, filed June 8, 1979, now abandoned.

SUMMARY OF THE INVENTION

This invention relates to a new method of producing the A-30912 antibiotics which comprises culturing *Aspergillus nidulans* var. *roseus*, NRRL 11440, under submerged aerobic fermentation conditions until a substantial level of antibiotic activity is produced. The A-30912 antibiotics are separated initially as a complex (the A-42355 antibiotic complex). A-30912 factors A, B, D, and H are isolated from the A-42355 complex by chromatography. The A-30912 antibiotics have antifungal activity.

This invention further relates to the biologically pure culture of the microorganism *Aspergillus nidulans* var. *roseus* which is useful for the production of the A-30912 antibiotics.

A-30912 factor A (antibiotic A-22082) and a method for its production using *Aspergillus nidulans* NRRL 8112 are described in U.S. Pat. No. 4,024,246; and A-30912 factors A, B, C, D, E, F, and G and a method for their production using *Aspergillus rugulosus* NRRL 8113 are described in U.S. Pat. No. 4,024,245. A-30912 factor H, a newly discovered minor factor of the A-30912 complex, is described in the co-pending application of Karl H. Michel entitled ANTIBIOTIC A-30912 FACTOR H, filed herewith this even date.

DESCRIPTION OF THE DRAWINGS

The infrared absorption spectrum of A-30912 factor H in KBr disc is presented in FIG. 1 of the accompanying drawings.

DETAILED DESCRIPTION

This invention relates to a new method of producing the A-30912 antibiotics. The A-30912 antibiotics are produced as a complex comprising several individual factors.

The term "antibiotic complex" as used in the fermentation art and in this specification refers to a mixture of co-produced individual antibiotic factors. As will be recognized by those familiar with antibiotic production by fermentation, the ratio of individual factors produced in an antibiotic complex will vary, depending on the fermentation conditions used.

The antibiotic complex of the present invention is arbitrarily designated herein as the A-42355 antibiotic complex. To avoid confusion, however, the A-30912 designations will be used for those individual factors of the A-42355 complex which are identical to A-30912 factors.

As is the case with the A-30912 antibiotic complex, A-30912 factor A is the major factor of the A-42355 antibiotic complex; A-30912 factors B, D, and H continue to be minor factors in the A-42355 complex.

The Prior Art

A-30912 factor A (antibiotic A-22082) is discussed in U.S. Pat. Nos. 4,024,245 and 4,024,246. At the time these patents issued, it was believed that A-30912 factor A might be different from echinocandin B [see F. Benz et al., *Helv. Chim. Acta* 57, 2459–2477 (1974) and Swiss Pat. No. 568,386 (Derwent Abstract 75884W)]. Later, evidence has shown that A-30912 factor A is identical to echinocandin B. Antibiotic SL 7810/F has also been identified as echinocandin B [C. Keller-Juslen, et al., *Tetrahedron Letters* 1976 (46), 4147–4150, and Belgium Pat. No. 834,289 (Derwent Abstract 30159X)].

Keller-Juslen, et al., proposed structure 1 for echinocandin B (SL 7810/F):

R = linoleoyl

Echinocandin B (antibiotic 32204) is produced by fermentation of a strain of *Aspergillus nidulans* var. *echinulatus* A 32204 (NRRL 3860), as discussed in Swiss Pat. No. 568,386 (Derwent No. 75884W). Antibiotic SL 7810/F is produced by a strain of *Aspergillus rugulosus*, Thom and Raper (NRRL 8039) as disclosed in Belgian Pat. No. 834,289 (Derwent No. 30159X). The method of this invention for producing A-30912 factor A (echinocandin B; SL 7810/F) by culturing *Aspergillus nidulans* var. *roseus* differs from the prior art methods. For convenience, the A-30912 factor A designations will be used herein to refer to this antibiotic.

A-30912 factors B and D are described in U.S. Pat. No. 4,024,245. A-30912 factor B is similar to, and may be identical to, antibiotic SL 7810/-II. A-30912 factor D is similar to, and may be identical to, antibiotic SL 7810/-III. Antibiotics SL 7810/-II and SL 7810/-III are produced by a strain of *Aspergillus rugulosus*, Thom and Raper (NRRL 8039) as disclosed in Belgian Pat. No. 834,289 (Derwent No. 30159X).

A-30912 Factor H

A-30912 factor H (A-30912H), the newly discovered component of the A-30912 antibiotic complex, is quite similar to A-30912 factor A. Under conditions known thus far, A-30912H is a minor factor in the A-30912 complex, being present in amounts in the range of from about 0.01 to about 1.0 percent of the total complex. Another minor factor of the A-30912 complex has been recognized, but has not been isolated in an amount sufficient for characterization. A-30912 factor H is best separated from this factor by silica-gel TLC using an ethyl acetate:methanol (3:2) or an acetonitrile:water (95:5) solvent system. In either system, the uncharacterized minor factor is more polar than the other A-30912 factors.

A-30912 factor H is a white amorphous solid. Elemental analysis of A-30912H gave the following approximate percentage composition: carbon, 58.27%; hydrogen, 7.49%; nitrogen, 8.67%; oxygen, 24.99%.

A-30912 factor H has a molecular weight of about 1073. This molecular weight is based upon peak matching (FD/FD) of the quasimolecular ions of A-30912 factor A ($C_{52}H_{81}N_7O_{16}$) and A-30912 factor H. The quasimolecular ion of A-30912 factor H (+Na) was found to have the mass 1096.5782, 1096.5814. The mean mass, 1096.5798, is within experimental error for $C_{53}H_{83}N_7O_{16}$.Na, which has a theoretical mass of 1096.57940.

The approximate empirical formula of A-30912 factor H is, therefore, believed to be $C_{53}H_{83}N_7O_{16}$. The elemental analysis of A-30912 factor H corresponds especially well with the empirical formula of $C_{53}H_{83}N_7O_{16}$·$H_2O$ (Calcd.: C, 58.30; H, 7.79; N, 8.98; O, 24.93).

Figure 1:
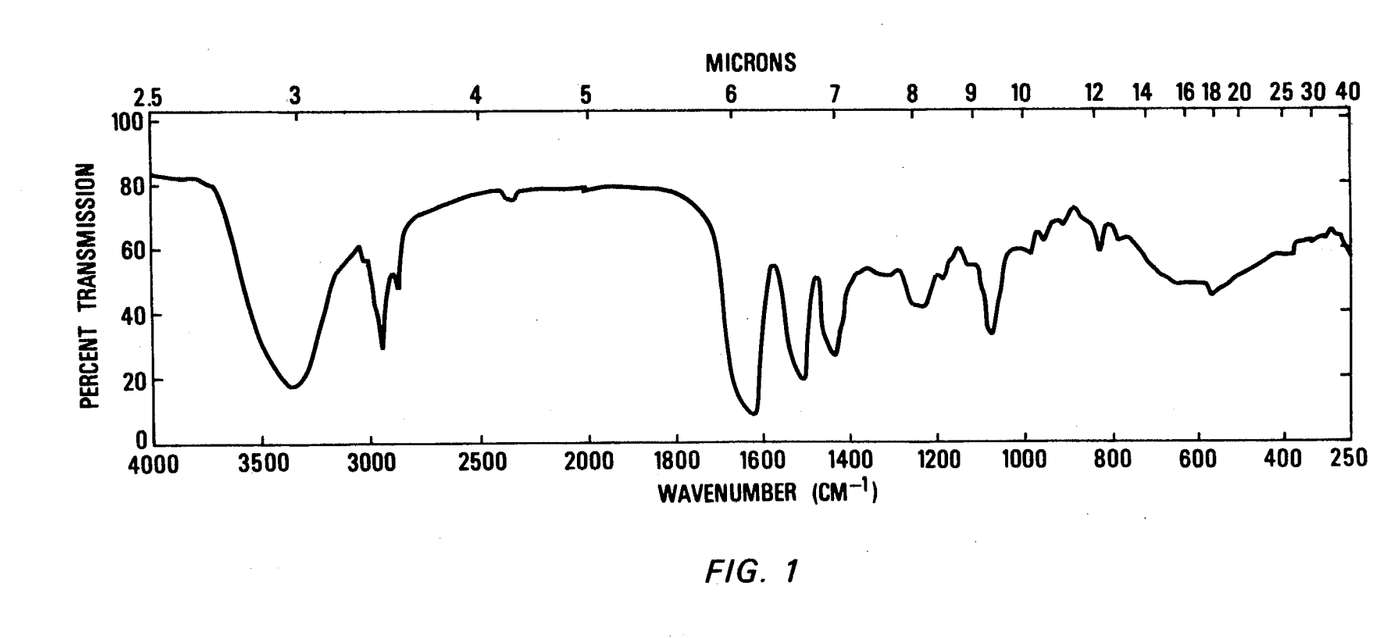

The infrared absorption spectrum of A-30912 factor H in KBr disc is shown in FIG. 1 of the accompanying drawings. The following characteristic absorption maxima are observed: 2.9 (very strong), 3.4 (strong), 3.5 (medium), 5.9–6.1 (very strong), 6.6 (strong), 6.9 (strong), 7.9–8.1 (medium), and 9.1 (strong) microns.

The ultraviolet absorption spectra of A-30912 factor H in both neutral and acidic methanol exhibit absorption maxima at 223 nm ($\epsilon$ 13,100) and 275 nm, broad peak ($\epsilon$ 2,100). The ultraviolet spectrum of A-30912 factor H in basic methanol shows absorption maxima at 245 nm ($\epsilon$ 14,700) and 290 nm, broad peak ($\epsilon$ 3,500), and also end absorption.

The $^{13}C$ nuclear magnetic resonance spectrum of A-30912 factor H in perdeuteromethanol shows the following characteristics:

δ 176.07, 174.15, 173.49, 172.56, 172.47, 169.88, 158.45, 133.01, 130.90, 129.52, 129.04, 116.21, 82.15, 77.00, 75.98, 75.71, 71.27, 69.55, 69.42, 68.22, 62.44, 58.69, 57.25, 56.81, 56.08, 52.88, 51.32, 39.08, 38.60, 36.89, 32.65, 30.77, 30.45, 30.26, 28.18, 27.14, 26.55, 20.11, 19.60, 11.33.

A-30912 factor H has the following approximate specific rotations:

$[\alpha]_D^{25}$ −40° (c 0.5, $CH_3OH$)
$[\alpha]_{365}^{25}$ −151° (c 0.5, $CH_3OH$)

Electrometric titration of A-30912 factor H in 66% aqueous dimethylformamide indicated the presence of a titratable group with a $pK_a$ value of about 12.90 (initial pH 7.12).

Amino acid analysis of A-30912 factor H indicated the presence, after hydrolysis, of threonine and four other as-yet-unidentified amino acids.

A-30912 factor H is soluble in a variety of organic solvents such as methanol, ethanol, dimethylformamide, dimethyl sulfoxide, and ethyl acetate; but is insoluble in nonpolar organic solvents such as diethyl ether and petroleum ether. A-30912 factor H is also soluble in aqueous solutions, especially those having a pH greater than 7.0.

A-30912 factor H (mol. wt. 1073) differs from A-30912 factor A (mol. wt. 1059) by only 14 mass units. Both compounds are very similar in physical-chemical properties, and both compounds produce linoleic acid upon hydrolysis. A-30912H has an additional —$CH_2$— which is present as —O—$CH_3$, replacing one of the —OH groups in the cyclic peptide portion of the molecule.

A-30912H has the structure shown in formula 2:

R = linoleoyl

The Microorganism

The method for producing the A-30912 antibiotics of this invention comprises cultivating, as herein described, a new culture which is a variety of *Aspergillus nidulans*. The new culture has been named *Aspergillus nidulans* var. *roseus*.

The new microorganism of this invention is a biologically pure culture which was isolated from a soil sample from Greenfield, Indiana. One of its strain characteristics is production of the A-30912 antibiotics. A subculture of this microorganism has been deposited and made a part of the permanent culture collection of the Northern Regional Research Laboratory, U.S. Department of Agriculture, Agricultural Research Service, Peoria, Illinois 61604, from which it is available to the public under the number NRRL 11440.

As is the case with other organisms, the characteristics of *Aspergillus nidulans* var. *roseus* NRRL 11440 are subject to variation. For example, artificial variants and mutants of the NRRL 11440 strain may be obtained by treatment with various known mutagens, such as ultraviolet rays, X-rays, high frequency waves, radioactive rays, and chemicals. All natural and artificial variants and mutants of *Aspergillus nidulans* var. *roseus* NRRL 11440 which retain the characteristic of production of the A-30912 antibiotics may be used in this invention.

Taxonomy of *Aspergillus nidulans* var. *roseus*

The new culture of this invention was studied and characterized by Thomas H. Sands of the Lilly Research Laboratories.

For convenience herein, the new culture *Aspergillus nidulans* var. *roseus* will be called culture A42355. The taxonomic basis upon which this culture is classified as a new variety of *Aspergillus nidulans* and named *A. nidulans* var. *roseus* is discussed in the following paragraphs. In this discussion, the terms "ISCC-NBS" refer to color names based on the ISCC-NBS method (K. L. Kelly and D. B. Judd, "The ISCC-NBS Methods of Designating Colors and A Dictionary of Color Names," U.S. Department of Commerce, Circ. 553, Washington, D.C., 1955). The term "Maerz and Paul" refers to color blocks described by A. Maerz and M. R. Paul in "Dictionary of Color," McGraw-Hill Book Company, New York, N.Y., 1950.

Comparisons are based on the work of K. B. Raper and D. I. Fennel, "The Genus Aspergillus," Williams and Wilkins, 1965.

Culture A42355 attains a diameter of 14 mm in seven days and 35 mm in 21 days when grown on Czapek's solution agar at 25° C. The colony surface is radially buckled, convex and initially velutinous to slightly floccose. The surface appearance changes with age due to the formation of a pink exudate that, after drying occurs, results in a pocked surface. The margin is strongly crenate to lobate and sharply delineated, showing only scant peripheral subsurface growth. As the colony ages, pigment variation causes a zonate effect. The reverse surface appears concave and in contact with the agar only in the periphery. A pink soluble pigment is produced. The mycelial mat is very tough and produces no distinctive odor. Pigmentation in young colonies is influenced by immature conidia which are light greenish yellow (ISCC-NBS 101 and Maerz and Paul 11-K-1). This color eventually is confined to the colony periphery. After 10 days, subspherical masses of Hülle cells encrusting blackish purple cleistothecia are scattered throughout the colony but are most noticeable clustered in the center. In 21 days, the narrow, slightly flattened margin is grayish greenish yellow (ISCC-NBS 105 and Maerz and Paul 12-I-2). Inside this margin, the colony is moderate yellowish pink (ISCC-NBS 29 and Maerz and Paul 11-A-6), and the color is influenced by the exudate. After 21 days, the center is darkened by grayish green conidia and hülle-cell-encrusted blackish purple cleistothecia. The reverse ranges from light brown (ISCC-NBS 57 and Maerz and Paul 13-A-7) to moderate reddish brown (ISCC-NBS 43 and Maerz and Paul 6-F-9). In three weeks or more, the reverse is in shades of very dark purple, nearly black.

The conidial head at first is radiate and bright yellow and then becomes dark green and tightly columnar. When mature, heads range from $93.4\mu$ to $116.7\mu$ long and have an average size of $106\mu \times 47\mu$. The vesicle is somewhat spathulate to pyriforme and, like the conidiophore, is light brown. Vesicles are fertile over the upper two-thirds and range in size from 10 to $12\mu \times 8$ to $10\mu$ (average size $9.2\mu \times 11.3\mu$). Conidiophores are sinuous, smooth and relatively thick-walled. They range in length from $88\mu$ to $112\mu$ (average $101\mu$). Although they range in width from 4 to $6\mu$, most are $6\mu$ wide.

Sterigmata are biseriate, hyaline to light brown and are smooth-walled. Primary sterigmata are nearly cuneiform. They are from $6.3\mu$ to $10.3\mu$ long and from $2\mu$ to $3\mu$ wide at their widest point (average size: $9.3\mu \times 2.7\mu$). Secondary sterigmata are between ovoid and obpyriform and range from $5.5\mu$ to $11.0\mu \times$ from $2.4\mu$ to $3.2\mu$ (average size: $9.9\mu \times 2.9\mu$). Conidia are globose, delicately roughened to echinulate and dark green. They range from 2.4 to $4.0\mu$ and average $3.2\mu$ in diameter.

On malt-extract agar at 35° C., a 14-mm diameter colony is produced in seven days. The colony diameter will achieve 30 mm in 21 days. Initially, the colony consists of white aerial hyphae. Conidiation occurs in the first week, and the relatively flat, velutinous, crenate colony becomes dark yellowish green (ISCC-NBS 137 and Maerz and Paul 24-J-6). The colony appears zonate due to concentric rings of yellow spherical masses of hülle cells that surround or encrust dark purple cleistothecia. The conidiogenous state on malt-extract agar resembles that state on Czapek's solution agar except for dimensions.

Conidial heads range in length from $100\mu$ to $170\mu$ and average $138\mu \times 50\mu$ in size. Conidiophores are from $100\mu$ to $210\mu$ long (average $182\mu$) and are $6\mu$ wide. Vesicles are from $8\mu$ to $12\mu \times$ from $6\mu$ to $12\mu$ (average size: $12\mu \times 9.2\mu$). Primary sterigmata are from $5.5\mu$ to $8.7\mu \times 2.4\mu$ to $4.0\mu$ (average size: $7.2\mu \times 6.6\mu$). Secondary sterigmata are $5.5\mu$ to $10.3\mu \times 2.0\mu$ to $3.6\mu$ (average size: $7.4\mu \times 3.5\mu$). Conidia are from 2.3 to $3.2\mu$, but average $3.2\mu$, in diameter.

The ascogenous state is similar on both agars. Numerous dark purple cleistothecia are encrusted with globose to subglobose, thick-walled, hyaline-to-pale-yellow hülle cells which are from $12.6\mu$ to $18.2\mu$ in diameter (average size: $15.3\mu$). Cleistothecia are globose to subglobose and have walls up to three layers thick, the outer layer consisting of pseudoparenchymatous cells. Cleistothecia range in diameter from $140\mu$ to $800\mu$, but are mostly $165\mu$ to $250\mu$ with an average diameter of $229\mu$. The eight-spored hyaline asci are globose to subglobose or irregularly ellipsoidal. When globose, they are $9.2\mu$ in diameter with little deviation from this size. Ellipsoidal asci are $9.3\mu \times 8.3\mu$. Ascospores are orange-red pigmented, globose in the surface view and lenticular in the lateral view. Two delicately pleated, entire, parallel equatorial crests are seen in the long axis of the lenticular view. In the surface view, a single crest is seen peripheral to the main spore body which is smooth and of bivalve construction. The crest is $0.5\mu$ wide; the spore body is $4.4\mu$ in diameter. The average lenticular view size is $4.7\mu \times 3.7\mu$.

Yellowish green regulose conidia, columnar conidial heads, smooth-walled light brown conidiophores and vesicles, biseriate sterigmata and the production of globose, thick-walled hülle cells place A42355 in the *Aspergillus nidulans* group. These characteristics, combined with the fact that the culture has an ascogenous state in which dark purple globose cleistothecia are closely associated with, or even encrusted with, hülle cells (as above) and has orange-red lenticular ascospores which are adorned with two pleated, parallel equatorial crests, place A42355 in the genus Emericella, the perfect state of the *A. nidulans* group.

A42355 does not fully fit the description of any of the published species or varieties in the *A. nidulans* group. The species most similar to A42355 is *A. nidulans* (Eidam) Wint., based on the type culture WB187 (NRRL 187). These cultures are similar in color and ascospore type, but differ in crest width. Cleistothecia are similar, but the wall of A42355 is a multilayer of cells instead of a single layer. Both cultures exhibit a yellow green, predominant conidial stage on malt-extract agar, but the ascogenous state of A42355 is more strongly evident than is that of the type culture where it is partially overgrown and is dully pigmented. In both cultures, the hyphae, conidiophores and vesicles are smooth-walled, without encrustment; however, the vesicle of A42355 is spathulate to pyriforme, whereas the vesicle of *A. nidulans* is hemispherical. Colonies of A42355 and *A. nidulans* when grown on Czapek's solution agar differ in growth rate, exudate production, abundance and size of conidial heads and in most other measured dimensions.

Although there are similarities between A42355 and *A. nidulans* (Eidam) Wint., there are sufficient significant differences that A42355 is considered a new variety which has been named *A. nidulans* var. *roseus*.

Cultivation of *A. nidulans* var. *roseus*

The culture medium used to grow *Aspergillus nidulans* var. *roseus* can be any one of a number of media. For economy in production, optimal yield and ease of product isolation, however, certain culture media are preferred. Thus, for example, a preferred carbon source in large-scale fermentation is cottonseed oil or glucose, although molasses, starch, dextrin, lactose, sucrose, maltose, glycerol, fatty acids and the like may be used. Preferred nitrogen sources are enzyme-hydrolyzed casein, soybean meal and soluble meat peptone, although distiller's grains, nitrate salts, monosodium glutamate and the like may be used. Nutrient inorganic salts can be incorporated in the culture media. These include the customary soluble salts capable of yielding sodium, magnesium, zinc, iron, calcium, ammonium, chloride, carbonate, sulfate, nitrate, phosphate, and the like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e., 0.2 ml/L) of an antifoam agent such as polypropylene glycol to large-scale fermentation media if foaming becomes a problem.

For production of a substantial quantity of the A-42355 antibiotic complex, submerged aerobic fermentation in tanks is preferred. Small quantities of the A-42355 antibiotic complex may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that used for larger fermentations, but other media can also be used.

*A. nidulans* var. *roseus* NRRL 11440 can be grown at temperatures betweeen about 20° and about 43° C.; the organism grows best at temperatures of about 30°–37° C. Optimum production of the A-30912 antibiotic complex occurs at temperatures below 30° C.

As is customary in aerobic submerged culture processes, sterile air is blown through the culture medium. For efficient antibiotic production, there should be sufficient aeration and agitation to maintain a dissolved oxygen level of at least 40% of air saturation at atmospheric pressure. Agitation is also helpful in breaking up the thick and heavy culture growth during the fermentation.

Production of the A-42355 antibiotic complex can be followed during the fermentation by testing samples of fermented broth or alcoholic extracts of the biomass or the whole broth for antibiotic activity against an organism known to be sensitive to the A-30912 antibiotics. One assay organism useful in testing for the presence of the A-30912 antibiotics is *Candida albicans*. The bioassay is conveniently performed by paper-disc or agar-well assay on seeded agar plates.

Generally, antibiotic activity can be detected by the second day of fermentation. Maximum production of antibiotic activity usually occurs between about the sixth and the eighth days.

Figure 2:
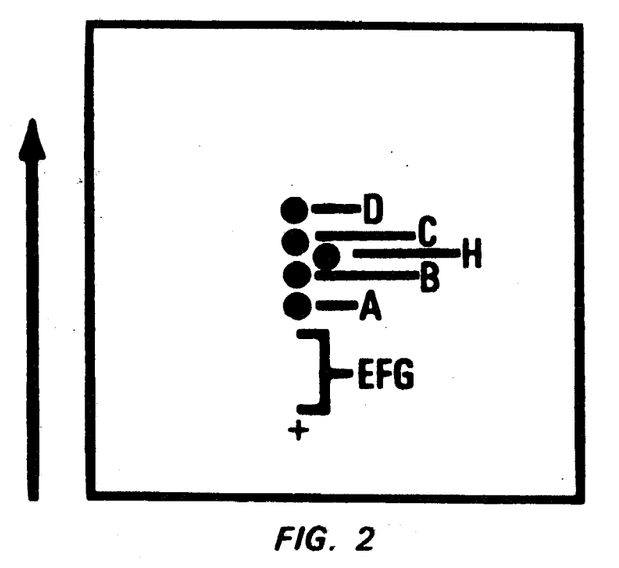
FIG. 2 of the accompanying drawings summarizes the relative movements of the A-30912 factors on thin-layer chromatography (TLC), using silica gel (Merck-Darmstadt) adsorbent, an ethyl acetate:methanol (3:2) solvent system, and *Candida albicans* bioautography for detection. The arrow indicates the direction of solvent flow; the "+" indicates the point of origin. The area where minor factors E, F, and G may be seen is indicated by bracketing. Specific $R_f$ comparisons between A-30912 factor A and minor factors E, F, and G are found in U.S. Pat. No. 4,024,245 (see Table I in column 4).

The individual A-30912 factors can be separated from the A-42355 complex and identified by the use of TLC (see FIG. 2 of the drawings). Silica gel is a preferred adsorbent.

The $R_f$ values of A-30912 factors A-G, using silica gel (Merck, Darmstadt) TLC, a benzene:methanol (7:3) solvent system, and *Candida albicans* bioautography are given in Table I.

TABLE I

| A-30912 Factor | $R_f$ Value |
| --- | --- |
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table II.

TABLE II

| A-30912 Factor | $R_f$ Values - Solvent Systems | | | |
| --- | --- | --- | --- | --- |
|  | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a: ethyl acetate:methanol (3:2)
b: ethyl acetate:methanol (7:3)
c: acetonitrile:water (95:5)
d: ethyl acetate:ethanol:acetic acid (40:60:0.25)

Recovery of the A-30912 Antibiotics

The A-30912 antibiotics can be recovered from the fermentation medium by methods known in the fermentation art. The A-30912 antibiotics generally occur in the mycelial portion of the fermentation medium. Maximum recovery is accomplished by extraction of the whole broth. It is preferable to add an equal volume of a solvent such as methanol to the whole broth and to lower the pH of the filtered broth to about pH 4–6 before extraction. Another method of isolation is to separate the mycelia, extract the mycelia with methanol, and recover the antibiotics by extraction of the methanolic extract. Chloroform is an expecially advantageous solvent for extracting A-30912 antibiotics as the A-42355 complex, although other such solvents may be used.

The individual A-30912 antibiotics may be isolated from the separated A-42355 complex by chromatography using various adsorbents. Suitable adsorbents include silica gel; reversed-phase resins such as silica gel/$C_8$, silica gel/$C_{18}$, Quantum LP-1, or LiChroprep RP-8 and RP-18; Florisil; Sephadex G-25, LH-20, and G-15; alumina; Diaion HP-20; Amberlite XAD-4 and X-384. Diaion is available from Mitsubishi Chemical Industries, Tokyo; the Amberlite resins are available from Rohm and Haas Co., Philadelphia, Pa.; the Sephadex resins are available from Pharmacia Fine Chemicals AB, Uppsala, Sweden; Florisil is available from Floridin Co., Tallahassee, Fla., and silica gel/$C_8$ and silica gel $C_{18}$ are available from E. Merck, Darmstadt, Germany. The preparation of a high loading capacity silica gel/$C_{18}$ from LP-1 silica gel (Whatman) is described in Example 8.

Reversed-phase high performance, low pressure liquid chromatography (HPLPLC) using silica gel/$C_{18}$ adsorbent is a preferred method for final purification of the A-30912 antibiotics. In this method, A-42355 complex (obtained, for example, by extraction of the filtered broth with chloroform), dissolved in solvent, is placed on a column equilibrated with the same solvent. The column is then eluted with the solvent. Methanol:water:acetonitrile (7:2:1) is a preferred solvent system. Fractions collected are monitored by *Candida albicans* bioautography and/or by UV (based on relative retention times). Fractions containing the desired A-30912 factor are combined. It is sometimes necessary to carry out an additional chromatographic separation in order to obtain the A-30912 factor in purified form.

A-30912 factors A, B, D and H can be separated by HPLPLC using the following conditions:

| Column: | glass, 0.8 × 15.0 cm |
| --- | --- |
| Packing: | Nucleosil ® 10-$C_{18}$ (Machery-Nagel and Company); packed using slurry-packing procedure of Example 8 |
| Solvent: | methanol:water:acetonitrile (7:2:1) |
| Sample Volume: | 8 mcl |
| Sample Size: | 8 mcg |
| Column Temperature | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table III.

TABLE III

| A-30912 Factor | Retention Time (seconds) |
| --- | --- |
| A | 792 |
| B | 870 |
| H | 990 |
| D | 1,140 |

In order to illustrate this invention more fully, the following examples are provided.

EXAMPLE 1

Preparation of the A-42355 Antibiotic Complex

A. Shake-Flask Fermentation

A culture of *Aspergillus nidulans* var. *roseus* NRRL 11440 is prepared and maintained on an 18-×150-ml agar slant prepared with medium having the following composition:

| Ingredient | Amount |
| --- | --- |
| Glucose | 5 g |
| Yeast extract | 2 g |
| $CaCO_3$ | 3 g |
| Vegetable juice* | 200 ml |
| Agar** | 20 g |
| Deionized water (initial pH 6.1) | q.s. to 1 liter |

*V-8 Juice, Campbell Soup Co., Camden, N.J.
**Meer Corp.

The slant is inoculated with *Aspergillus nidulans* var. *roseus* NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount |
| --- | --- |
| Sucrose | 25 g |
| Blackstrap molasses | 36 g |
| Corn-steep liquor | 6 g |
| Malt extract | 10 g |
| $K_2HPO_4$ | 2 g |
| Enzymatic hydrolysate of casein* | 10 g |
| Tap water (initial pH 6.5–6.7) | 1100 ml |

*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows:

The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

MEDIUM I

| Ingredient | Amount |
| --- | --- |
| $ZnSO_4 \cdot 7H_2O$ | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| $Na_2HPO_4$ | 4.5 g/L |
| $MgSO_4 \cdot 7H_2O$ | 5.5 g/L |
| $FeSO_4 \cdot 7H_2O$ | 0.1 g/L |
| Cottonseed oil | 40.0 ml |
| (Antifoam)**** | 1.0 ml |
| Tap water (initial pH 6.8–7.0) | 1000.0 ml |

*O.M. Peptone, Amber laboratories, Juneau, Wisc.
**Stadex 11, A.E. Staley Co., Decatur, Ill.
***N-Z-Amine A, Humko Sheffield Chemical, Lyndhurst, N.J.
****P2000, Dow Corning, Midland, Mich.

MEDIUM II

| Ingredient | Amount |
| --- | --- |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 \cdot 7H_2O$ | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
| --- | --- |
| Sucrose | 25 g |
| Blackstrap molasses | 25 g |
| Corn-steep liquor | 6 g |
| Enzymatic hydrolysate of casein* | 10 g |
| Malt extract | 10 g |
| $K_2HPO_4$ | 2 g |
| Tap water | 1000 ml |
| (initial pH 6.1) | |

*N-Z-Case

EXAMPLE 2

Separation of the A-42355 Antibiotic Complex

Whole fermentation broth (4127 liters), obtained by the method described in Example 1 using production medium II, was stirred thoroughly with methanol (4280 liters) for one hour and then was filtered, using a filter aid (Hyflo Super-cel, a diatomaceous earth, Johns-Manville Products Corp.). The pH of the filtrate was adjusted to pH 4.0 by the addition of 5 N HCl. The acidified filtrate was extracted twice with equal volumes of chloroform. The chloroform extracts were combined and concentrated under vacuum to a volume of about 20 liters. This concentrate was added to about 200 liters of diethyl ether to precipitate the A-42355 complex. The precipitate was separated by filtration to give 2775 g of the A-42355 complex as a gray-white powder.

EXAMPLE 3

Isolation of A-30912 Factor A

A-42355 antibiotic complex (1 g), prepared as described in Example 2, was dissolved in 7 ml of methanol:water:acetonitrile (7:2:1). This solution was filtered and introduced onto a 3.7-cm I.D.×35-cm glass column [Michel-Miller High Performance Low Pressure (HPLPLC) Chromatography Column, Ace Glass Incorporated, Vineland, NJ 08360] packed with LP-1/$C_{18}$ silica gel reversed-phase resin (10–20 microns), prepared as described in Example 7, through a loop with the aid of a valve system. The column was packed in methanol:water:acetonitrile (7:2:1) by the slurry-packing procedure described in Example 8. An F.M.I. pump with valveless piston design (maximum flow 19.5 ml/minute) was used to move the solvent through the column at a flow rate of 9 ml/minute at ca. 100 psi, collecting fractions every minute. Elution of the antibiotic was monitored at 280 nm by using a UV monitor (ISCO Model UA-5, Instrument Specialist Co., 4700 Superior Ave., Lincoln, Nebraska 68504) with an optical unit (ISCO Type 6).

Fractions 112–140 were combined and added to 20 ml of water. The pH of this solution was adjusted to pH 4.0 with N HCl. The resulting solution was extracted twice with equal volumes of chloroform. The two chloroform extracts were combined and concentrated under vacuum to give an oil. The oil was dissolved in tertiary butanol, and this solution was lyophilized to give 524 mg of A-42355 factor A (A-30912 factor A; A-22082).

EXAMPLE 4

Isolation of A-30912 Factor B

A-42355 complex was separated as described in Example 2 except that the concentrated chloroform extracts (285 L) were chromatographed over a silica-gel column (150 L of Grace silica-gel, grade 62) at a flow rate of 2 L/min. The column was washed with chloroform (200 L), eluted with acetonitrile (500 L), and then continuously eluted with acetonitrile:water (98:2) at a flow rate of 1 L/min. Fractions having a volume of approximately 200 L were collected and analyzed individually for biological activity. The bioassay was performed by a paper-disc assay on agar plates seeded with *Candida albicans*. Fractions 77 through 103 (1365 L) were combined and concentrated under vacuum. The concentrated solution (4.5 L) contained a precipitate which was removed by filtration to give 119 g of factor B-enriched A-42355 complex. The filtrate was concentrated to dryness; the residue obtained was redissolved in an appropriate volume of methanol. The methanol solution was added to diethyl ether (10 volumes) to precipitate the factor-B-containing antibiotic complex. This precipitate was also separated by filtration and dried to give an additional 24 g of factor-B-enriched A-42355 complex as a gray powder.

Factor-B-enriched A-42355 complex thus obtained (1.0 g) was dissolved in 8 ml of methanol:water:acetonitrile (7:2:1). This solution was filtered and introduced onto a silica-gel column (3.7-cm I.D.×33-cm Michel-Miller Column) through a loop with the aid of a valve system. The column was packed with LP-1/$C_{18}$ silica-gel reversed-phase resin (10–20 microns) in methanol:water:acetonitrile (7:2:1) as described in Example 3. The solvent was moved through the column at a flow rate of 10 ml/min at ca. 100 psi as in Example 3. One fraction was collected every minute. Elution of the antibiotic was monitored at 280 nm as in Example 3. Fractions 102–110 were combined and concentrated under vacuum to give an oil. The oil was dissolved in a small volume of tert-butanol and lyophilized to give 22 mg of A-30912 factor B.

EXAMPLE 5

Isolation of A-30912 Factor D

Concentrated chloroform extracts from two fermentation runs (3800 L and 4007 L) obtained by the method described in Example 1 were combined and chromatographed on a silica-gel column as described in Example 4. Fractions having a volume of approximately 200 L were collected and subjected to bioassay as in Example 4. Fractions 47–63 (850 L) were combined and concentrated under vacuum. The concentrated solution (0.7 L) was added to diethyl ether (10 volumes) to precipitate the factor D-enriched A-42355 complex. This precipitate was removed by filtration and dried to give 32 g of factor D-enriched A-42355 complex as a gray powder.

Factor D-enriched A-42355 complex thus obtained (1.0 g) was dissolved in 5 ml of methanol:water:acetonitrile (7:2:1). This solution was filtered and introduced onto a silica-gel column (3.7-cm I.D.×30-cm Michel-Miller Column) through a loop with the aid of a valve system. The column was packed with LP-1/$C_{18}$ silica-gel reversed-phase resin (10–20 microns). Packing was accomplished in methanol:water:acetonitrile (7:2:1) as described in Example 3. The solvent was moved through the column at a flow rate of 8 ml/min at ca. 45 psi as described in Example 3. One fraction was collected every 2 minutes. Elution of the antibiotic was monitored at 280 nm as described in Example 3. Fractions 96–108 were combined and concentrated under vacuum to give an oil. This oil was dissolved in a small volume of tert-butanol and lyophilized to give 89 mg of A-30912 factor D.

EXAMPLE 6

Isolation of A-30912 Factor H

A-42355 antibiotic complex (5.0 g), prepared as described in Example 2, was dissolved in 35 ml of methanol:water:acetonitrile (7:2:1); the resulting solution was filtered and introduced onto a 3.7-cm I.D.×42-cm glass column (Michel-Miller Column) through a loop with the aid of a valve system. The column was packed with LP-1/$C_{18}$ silica gel reversed phase resin (10–20 microns) in methanol:water:acetonitrile (7:2:1) as described in Example 3. The solvent was moved through the column at a flow rate of 13 ml/min at ca. 120 psi as described in Example 3, collecting one fraction every two minutes. Elution of the antibiotic was monitored at 280 nm as described in Example 3. Fractions 112–132 were combined with fractions 106–117 from a second similar purification. The combined fractions were concentrated under vacuum to an oil. The oil was dissolved in a small volume of tert-butanol and lyophilized to give 173 mg of crude A-30912 factor H.

The crude A-30912 factor H (150 mg) was dissolved in 8 ml of methanol:water:acetonitrile (7:2:1); the resulting solution was filtered and introduced onto a 2.0-cm I.D.×32-cm glass column, as described above. The solvent was moved through the column at a flow rate of 8 ml/min at ca. 80 psi as described in Example 3, collecting one fraction every three minutes. Elution of the antibiotic was monitored at 280 nm as described in Example 3. Fractions 17 and 18 were combined and concentrated under vacuum to give an oil. The oil was dissolved in a small volume of tert-butanol and lyophilized to give 29 mg of A-30912 factor H.

EXAMPLE 7

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azetrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring care-

EXAMPLE 8

Slurry Packing Procedure for Michel-Miller Columns

General Information

A. Analytical or preparative columns can be packed by this procedure.

B. Silica gels and silica gel reversed phase packings (e.g., Quantum LP-1, particle size 10–20 microns; Li-Chroprep RP-8 and RP-18, particle size 25–40 microns) are recommended. However, other silica gels (e.g., Shandons ODS Hypersil, particle size 5 microns) as well as other types of resins have been packed successfully by this procedure.

C. Generally, a pressure of less than 200 psi and flow rates between 5–40 ml/minute are required for this slurry packing technique; this is dependent on column volume and size. PLEASE NOTE: Packing pressure should exceed pressure used during actual separation by 30–50 psi; this will assure no further compression of the adsorbent during separation runs. Columns packed by this procedure with reversed-phase silica gel can be operated for several years without loss of efficiency.

D. Sudden decrease in pressure may cause cracks or channels to form in the packing material, which would greatly reduce column efficiency. Therefore, it is important to let the pressure drop slowly to zero whenever the pump has been turned off.

E. Approximate volume of columns (Ace Glass Cat. No., unpacked): 5795-04, 12 ml; 5795-10, 110 ml; 5795-16, 300 ml; 5795-24, 635 ml; and 5796-34, 34 ml.

F. The time required to pack a glass column will vary from minutes to several hours depending on column size and experience of the scientist.

Example

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant.

5. Slurry the resin with sufficient solvent to fill reservoir column. Pour swiftly into reservoir. NOTE: The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure.

NOTE: Always allow pressure to decrease slowly after turning off pump—this will prevent formation of any cracks or channels in the packing material.

10. Relieve pressure and disconnect pre-column carefully. With small spatula remove a few mm (2–4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

We claim:

1. The method of producing the A-42355 antibiotic complex comprising A-30912 factors A, B, D, and H which comprises cultivating *Aspergillus nidulans* var. *roseus* NRRL 11440 in a culture medium containing assimilable sources of carbohydrate, nitrogen, and inorganic salts under submerged aerobic fermentation conditions until a substantial amount of antibiotic activity is produced.

2. The method of claim 1 which includes the additional step of separating the A-42355 antibiotic complex from the culture medium.

3. The method of claim 2 which includes the additional step of isolating A-30912 factor A from the separated A-42355 antibiotic complex.

4. The method of claim 2 which includes the additional step of isolating A-30912 factor B from the separated A-42355 antibiotic complex.

5. The method of claim 2 which includes the additional step of isolating A-30912 factor D from the separated A-42355 antibiotic complex.

6. The method of claim 2 which includes the additional step of isolating A-30912 factor H from the separated A-42355 antibiotic complex.

7. A biologically pure culture of the microorganism *Aspergillus nidulans* var. *roseus* NRRL 11440 said culture being capable of producing the A-42355 antibiotic complex comprising A-30912 factors A, B, D and H.

* * * * *